US009215998B2

(12) United States Patent
Reinhold, Jr. et al.

(10) Patent No.: US 9,215,998 B2
(45) Date of Patent: Dec. 22, 2015

(54) DEVICE FOR OBTAINING A STANDARD 12-LEAD ELECTROCARDIOGRAM AND A RHYTHM STRIP

(71) Applicant: SHL Telemedicine International Ltd., Tel Aviv (IL)

(72) Inventors: Herbert E. Reinhold, Jr., Arnold, MD (US); Shay Leibovitz, Tel Aviv (IL); Roni Kazaz, Rishon Lezion (IL)

(73) Assignee: SHL Telemedicine International Ltd., Tel Aviv (IL)

( * ) Notice: Subject to any disclaimer, the term of this patent is extended or adjusted under 35 U.S.C. 154(b) by 11 days.

(21) Appl. No.: 14/085,165

(22) Filed: Nov. 20, 2013

(65) Prior Publication Data

US 2014/0081118 A1   Mar. 20, 2014

Related U.S. Application Data

(63) Continuation-in-part of application No. PCT/IL2012/000200, filed on May 21, 2012.

(60) Provisional application No. 61/488,913, filed on May 23, 2011.

(51) Int. Cl.
*A61B 5/044* (2006.01)
*A61B 5/00* (2006.01)
(Continued)

(52) U.S. Cl.
CPC ............. *A61B 5/6898* (2013.01); *A61B 5/0006* (2013.01); *A61B 5/0022* (2013.01); *A61B 5/0404* (2013.01); *A61B 5/044* (2013.01); *A61B 5/04085* (2013.01); *A61B 5/486* (2013.01); *A61B 5/6823* (2013.01);
(Continued)

(58) Field of Classification Search
CPC .. A61B 5/0402; A61B 5/0408; A61B 5/0432; A61B 5/0006; A61B 5/6898; A61B 5/0404; A61B 5/0022
USPC .................................................. 600/509, 523
See application file for complete search history.

(56) References Cited

U.S. PATENT DOCUMENTS

| 7,266,405 B1 * | 9/2007 | Alroy ................. A61B 5/04085 600/386 |
| 2005/0165319 A1 * | 7/2005 | Brodnick et al. ............. 600/509 |

(Continued)

OTHER PUBLICATIONS

International Search Report/Written Opinion, issued Oct. 1, 2012, in corresponding International Patent Application No. PCT/IL2012/000200, filed May 21, 2012.

*Primary Examiner* — Theodore Stigell
*Assistant Examiner* — Michael Carey
(74) *Attorney, Agent, or Firm* — Patrick J. Hagan; Dann, Dorfman, Herrell and Skillman, P.C.

(57) ABSTRACT

A device for obtaining a standard 12-lead ECG and a rhythm strip, comprising: a personal ECG device to which nine skin monitoring electrodes are electrically connected, either directly or via an electrodes belt and which presents an array of at least 6 precordial electrodes that are anatomically positioned for the user, two belt mounted limb electrodes and one flying electrode, such that the skin monitoring electrodes deployed on the belt in combination with those directly connected to the personal ECG device permit the acquisition of ECG data for the rhythm strip and the standard 12 lead ECG, and wherein the ECG device includes a communication module for transferring the ECG data to a remote data center via a mobile device.

7 Claims, 10 Drawing Sheets

(51) Int. Cl.
*A61B 5/0404* (2006.01)
*A61B 5/0408* (2006.01)

(52) U.S. Cl.
CPC ............ *A61B 5/6824* (2013.01); *A61B 5/6828* (2013.01); *A61B 5/6831* (2013.01); *A61B 5/7221* (2013.01); *A61B 5/7465* (2013.01); *A61B 5/7475* (2013.01)

(56) References Cited

U.S. PATENT DOCUMENTS

2008/0234592 A1* 9/2008 Lim et al. ...................... 600/509
2011/0105928 A1* 5/2011 Bojovic ................. A61B 5/046
　　　　　　　　　　　　　　　　　　　　　　600/515

* cited by examiner

Electrodes Positioning

DEVICE FOR OBTAINING A STANDARD 12-LEAD ELECTROCARDIOGRAM AND A RHYTHM STRIP

CROSS-REFERENCE TO RELATED APPLICATIONS

This application is a continuation-in-part of International Application No. PCT/IL2012/000200, filed May 21, 2012, which claims the benefit of U.S. Provisional Application No. 61/488,913, filed May 23, 2011. The entire disclosure of each of the aforesaid applications is incorporated by reference in the present application.

FIELD OF THE INVENTION

The present invention relates to the field of telemedicine systems. More particularly, the invention relates to a method and system for capturing a personal standard 12 lead ECG and rhythm strip data from a non-medical user remotely using a telecommunication mobile device, such as iPhone.

BACKGROUND OF THE INVENTION

It is known that chronically ill, people or patients known to suffer from cardiac problems, and patients recovering from a surgical intervention or cardiac episode or a disease use personal ECG devices whether this on regular basis or while they don't feel well. In the prior art there are several ECG devices that can obtain a standard 12 lead ECG, such as clinical ECG machines as well as personal ECG telephonic acoustic devices (e.g., CardioSenC, Cardiobeeper 12L or CardioBeeper 12/12 by SHL Telemedicine). These personal medical ECG devices are adapted to be used by a non-medical individual to capture a 12 lead ECG and/or Rhythm strip when the user has symptoms, routinely, as part of drug studies, pre/post surgery, etc. Although these devices do allow a non medical user to obtain a standard 12 lead ECG and rhythm strip at any time and transfer it to a remote medical data center, no ECG information is available for the user itself and the telephonic transmission acoustic devices are subject to local ambient noise that causes ECG interference.

The standard 12 lead electrocardiogram in clinical use today obtains the electrical activity of 9 monitoring electrodes and developing 12 views of the electrical activity in accordance with the accepted measuring methods as setforth by Einthoven, Goldberger and Wilson. Einthoven defined the Einthoven triangle by measure 3 limb leads consisting of the Right Arm (RA), Left Arm (LA) and Left Leg (LL). Goldberger further suggested the 3 augmented unipolar limb leads of aVR, aVL, and aVF which are measured sequentially by combining two limb leads and measuring the third limb. Wilson devised the summation of the three limb leads and measuring the electrical activity from 6 precordial anatomically positioned chest electrodes creating the views, V1, V2, V3, V4, V5, and V6. It is the use of these 12 leads that define the clinically accepted standard for today's 12 lead electrocardiogram.

Moreover, some of the prior-art personal devices, such as the Cardiosen'C that in addition to acoustic telephonic transmission can communicate with a remote data center directly via its internal cellular modem. However, this takes considerable power thus a large rechargeable battery and charger is also required resulting in a device having relatively large dimensions affecting its portability and less comfortable an unlikely to carry by the user at all times due to their overall dimensions. Therefore, there is also a need for a smaller device than the Cardiosen'C and the other prior-art units that utilize a smaller battery that device is easier to carry and therefore it is more desirable to be carried more often.

For years, many have tried to reduce the number of electrodes applied by placing fewer electrodes and recreating the 12 Lead ECG by calculation. All of these methods have some form of errors when compared to all the 12 Lead ECG from all people. Different anatomical masses, physical positions, changing conditions in the human body, inaccurate or improper electrode positioning together with calculation errors in the algorithms can contribute to errors and poor results. Steps have been taken to minimize errors including those set forth by some of the following prior art publications.

US patent application No. 2006/0111640 of Shen et al discloses an electrocardiogram monitoring device that utilizes a belt with 3 electrodes positioned in a non-standard position for creating a rhythm strip which can be wirelessly transmitted. This application does not disclose the proper method of acquiring the standard 12 lead ECG using the accepted standards setforth by Einthoven, Goldberger and Wilson.

US patent application No. 2009/0264782 of Perlman discloses a method of positioning sensors to derive synthetic composite electrocardiac signals from special sensors not positioned in the standard anatomical positions. However, this application does not disclose the measurement of the standard 12 lead ECG from the electrode placement as setforth by Einthoven and Goldberger nor the simultaneous acquisition of a rhythm strip which displays one or more views of a 12 lead ECG over time which can thus show changes in heart rhythm over time.

US patent application No. 2010/0069735 of Berkner discloses a non-conventional method of deriving a 12 lead ECG with a fewer number of electrodes and by progressively moving a handheld electrode to various locations on the body. To overcome positioning errors, it also discloses the need to calibrate electrode positions and an electronic positioning system without stating accuracy or performance. It also indicates detection of possible signal quality of one roving precordial electrode which is moved across the chest. However, this method is very prone to errors due to mispositioning of the electrodes plus the errors in recalculation and derivation of a 12 lead ECG. Moreover, it does not suggest the simultaneous detection of the quality of all the six precordial and 3 limb contacts necessary for the standard 12 lead ECG. While this application discloses the use of handheld electrodes without revealing the level of noise which is typically induced through the use of handheld electrodes and which is typically not encountered by using a stretchable belt to hold that electrodes in contact without utilizing the muscles of the hand and arm. The use of handheld electrodes and precise positioning by a non-medical user when experiencing acute symptoms of a heart attack is problematic and can lead to measurement errors.

US patent application No. 2011/0105928 of Bojovic et al disclose a wearable belt or belts with electrodes that position a limited numbers in a non-standard orthogonal position so a 12 lead ECG can be calculated and derived from 3 monitoring leads. However, the positioning of these electrodes are not the accepted positions for the standard 12 lead ECG as set forth by Einthoven, Goldberger and Wilson. Moreover, reconstruction of 12 lead ECGs have errors due to the algorithm process and such errors are well described in literature. To minimize errors, one method that has been in this disclosure, is to calibrate the data from the non-standard placement of this limited electrode device by simultaneously utilizing a standard clinical 12 lead ECG machine. The differences in the 12 lead ECGs obtained between the two devices are preserved and corrections are applied when future transmissions are made from the non-standard, limited electrode device in order to enhance the construction of a representative 12 lead ECG. Although this method may help to minimize some errors in the derived ECG however it is not the a clinical 12 lead ECG obtained from the standard anatomically positioned electrodes prescribed locations as set forth by Einthoven, Goldberger and Wilson. Therefore, such an arrangement may produce model and computational errors in the reconstruction of the standard 12 lead ECGs. This method requires a calibration procedure which is not only inconvenient for users but adds unnecessary additional costs. Furthermore, a wireless access point is disclosed to which the ECG device transmits, but this application does not utilize the capabilities of a mobile device such as a smartphone to retransmit the data to a remote location nor does it suggest the convenient display of the 12 lead ECG report or instructions, contact quality, etc. on the access point.

U.S. Pat. No. 4,608,987 of Mills discloses a vest of multiple sizes small, medium, large, etc. that is worn over the chest, back and shoulders that does position the electrodes in accordance with the standard 12 lead ECG electrode placements and is coupled with an acoustic device for telephone transmission to a remote location, however it does not suggest reducing the size of the vest to be a compact belt for portability and compact storage nor does he suggest a digital wireless means to transmit to a remote location eliminating possible acoustic noise.

US patent application No. 2005/0165319 of Brodnick et al discloses a method wherein a wireless phone establishes ECG data communication while in voice contact to transmit. The ECG signals are acquired through the use of a standard clinical ECG machine and a plurality of electrodes by someone with medical knowledge at undisclosed body locations and the data is transmitted to a remote location via internal wireless communication device such as a wireless telephone or connected to an external wireless module for transmission to a remote location. Although this application does suggest using a 12 lead clinical ECG machine that is used in hospital, clinics, etc. to acquire and interface with his device, he does not suggest any method for properly positioning electrodes for obtaining the standard 12 lead ECG data nor any means to transmit the data wirelessly using low power to a local cellular device (e.g., a smartphone) for retransmission to a remote facility. Nor does he suggest how such a device could be made in a small compact form to be easily carried by a user or be applied by the user to properly position the multiple electrodes for a standard 12 lead ECG without errors.

US patent application No. 2010/0124920 of Feher discloses a way to receive Bluetooth ECG signals and transmit to a remote location. However, this application does not specifically disclose a concept of displaying a standard 12 lead ECG nor a display of a representation ECG signals on the receiving/transmitting device itself.

US patent application No. 2008/0234592 of Lim et al discloses a handheld cardiac monitor with externally mounted electrodes. This device is a handheld box with finger electrodes on the housing. For lead I, the left and right hand fingers touch the electrodes. For lead II, the right hand finger can touch one electrode and the other left electrode can be held to the abdomen or the electrode can be removed from the box as it is extendable and positioned in the lead II position. There is no description or claim for obtaining a standard clinical 12 lead electrocardiogram. Moreover, it does not disclose a method for internally storing an electrode in a compact manner. Although it is disclosed that one terminal may also be an "extendable and retractable" lead relative to the housing, however no details of the manner of storage or retraction are revealed and thus the statements are too vague.

U.S. Pat. No. 7,266,405 of Alroy et al discloses a disposable, adhesive array that is not reusable nor is it always attached to the device which can be a problem in an emergency situation as there is no guarantee that this type of detachable array would always be immediately present for use with an electronic device particularly in an emergency situation. This array has at least 9 electrodes with moisture based electrode gel that must retain moisture in storage and is available in multiple sizes to accommodate gender and chest sizes.

In the prior art, U.S. Pat. Nos. 5,339,823, No. 5,465,727 and US patent application No. 2003/0187363 disclose a method and apparatus for a personal device to be used by an individual without any special medical training to capture and transmit a standard 12 lead electrocardiogram. These patents disclose the use of two flying electrodes, one for the right arm (RA) and the other left leg (LL). In emergency and routine use, it is possible to transpose these electrodes and thus acquire an erroneous 12 lead electrocardiogram. Further disclosed is a method of transmitting the ECG over a telephone by frequency modulating (FM) an audible carrier signal and acoustically coupling the sound to a telephone for transmission to a remote receiving location. FM acoustic device systems of this type however suffer from interference caused by local ambient sounds at the telephone as the signal being coupled to the phone. Further, any real-time changes in propagation time over the telephone system can affect the FM signal as received. The result of these transmission conditions adversely manifest as noise on the resulting ECG tracing at the receiving site.

However, although some of these prior art ECG devices are capable of transmitting data to remote medical data center, there still exists a need for a device that can be quickly and accurately applied to obtain a clinical 12 lead ECG and rhythm strip report as setforth by Einthoven, Goldberger and Wilson (i.e., the gold standard). There also still exists a need for such a system which is reliable in use and is user-friendly. There further exists a need for a personal ECG device which can be used in combination with existing portable computer based communication devices (e.g., a mobile cellphone or a smartphone) for enhancing the interaction between the remote medical data center the personal ECG device and the user itself.

It is an object of the present invention to overcome the drawbacks of the personal prior-art standard 12 lead ECG devices and to fulfill the aforementioned needs. The present invention is particularly aimed at ill, people or patients known to suffer from cardiac problems, patients recovering from a surgical intervention or cardiac episode, patients who are experiencing symptoms of arrhythmia, heart attack, ischemia, etc.

It is another object of the present invention to provide a system which is capable of remotely communicated with a data center.

It is yet another object of the present invention to provide a system which is capable of locally displaying ECG related activity information to the user including the quality of the electrode contact and other relevant information (e.g., guiding and instructions for the user during and/or after the use).

Other objects and advantages of the invention will become apparent as the description proceeds.

SUMMARY OF THE INVENTION

The present invention relates to a method for obtaining a standard 12-lead electrocardiogram and a rhythm strip, comprising:

a. capturing, by a personal ECG device, information related to the electrical activity of a user's heart as acquired from at least 9 skin monitoring electrodes positioned on the body of said user in a standard 12 lead anatomical manner in accordance with Einthoven, Goldberger and Wilson, wherein said standard 12 lead anatomical manner is obtained by deploying said electrodes along a belt connected with said ECG device and on the rear side of said ECG device, wherein at least some of said skin electrodes are precordial electrodes that are located on the inside of said belt and are positioned on the chest of said user, 2 electrodes are belt mounted limb electrodes located on the outside of said belt to acquire electrical signals of the left arm (LA electrode) and the right arm (RA electrode), and 1 flying electrode (LL electrode) to acquire the electrical signals of the left leg of said user;

b. generating ECG data, by said personal ECG device, for obtaining said standard 12-lead electrocardiogram in accordance with Einthoven, Goldberger and Wilson and said rhythm strip, wherein said generated ECG data represent the electrical activity of the heart of said user as acquired by said skin electrodes; and c. transferring said ECG data via a short range data communication wireless protocol to a paired mobile device, such as a smartphone, adapted to communicate with a remote data center for retransmitting said transferred ECG data to said remote data center; and d. processing said forwarded ECG data and creating a 12 lead ECG and Rhythm strip report at said remote data center, wherein said mobile device further adapted to receive said created 12 lead and rhythm strip report from said remote data center.

According to an embodiment of the invention, the mobile device establishes data communication with the remote data center for transmitting the ECG data while in voice contact with a representative of said remote data center.

According to an embodiment of the invention, the method further comprises forwarding from the remote data center the created 12 lead and rhythm strip report via one or more communication protocols to mobile devices, remote terminal units, portable computer based communication devices and other computer systems, thereby allowing said ECG data to be reviewed, stored and/or printed by medical professionals and others.

According to an embodiment of the invention, the method further comprises enabling the user to observe a representation of the 12 lead ECG and the rhythm strip report on the display of the mobile device.

According to an embodiment of the invention, the method further comprises improving electrode contact quality by using the mobile device to display to the user the quality of each ECG electrode contact, thereby providing feedback to the user to evaluate the quality of the electrode contact and permit said user to improve the contact and thus the quality of the resulting ECG.

According to an embodiment of the invention, the method further comprises providing instructions, questions, or other relevant data to the user while operating the personal ECG device, via the paired mobile device.

According to an embodiment of the present invention, the method further comprises forwarding the ECG data via one or more error checking communication protocols to a remote terminal unit, thereby, for example, allowing said ECG data to be reviewed at remote site by a medical stuff or other professional user. The mobile communication device can transmit the ECG data to any destination in real-time (or near real-time).

According to an embodiment of the present invention, the personal ECG device transmits 8 sample (e.g., of 2.5 second) views of the heart which commonly defined as lead I, II, V1, V2, V3, V4, V5, V6, and in addition it transmits the Rhythm strip (lead II). An exemplary set of electrodes for these leads is shown and described with respect to FIGS. 5 and 6 hereinafter.

In another aspect, the present invention relates to an electrocardiographic monitoring system, comprising:

a. a personal ECG device for obtaining standard 12-lead electrocardiogram (ECG) data in accordance with Einthoven, Goldberger and Wilson and wherein said ECG data represents the electrical activity of a user's heart;

b. a set of at least 9 skin monitoring electrodes that are deployed on a belt attached to said personal ECG device and to the rear side of said ECG device, such that said electrodes are automatically positioned at the standard anatomical electrode locations for acquiring said standard 12-lead ECG, wherein at least some of said skin electrodes are precordial electrodes that are located on the inside of said belt and are positioned on the chest of said user, 2 electrodes are belt mounted limb electrodes located on the outside of said belt to acquire electrical signals of the left arm (LA electrode) and the right arm (RA electrode), and 1 flying electrode (LL electrode) to acquire the electrical signals of the left leg of said user;

c. a short range wireless communication module embedded within said personal ECG device for data communicating with a paired mobile device, thereby allowing to transfer said ECG data from said personal ECG device to said mobile device; and d. a dedicated application for being executed by said mobile device for data communicating with a remote data center in order to transmit said transferred ECG data to said remote data center for processing said ECG data and creating a 12 lead ECG and Rhythm strip report, and for visually displaying information related to said created 12-lead ECG report as received from said remote center.

According to an embodiment of the invention, the belt is a chest strap electrode belt on which the skin electrodes are anatomically positioned and wherein said belt having a closure containing electrical connections that electrically connects at least some of said skin electrodes to the personal ECG device.

According to an embodiment of the invention, the personal ECG device and the belt comprise corresponding mechanisms which allows the replacing of the electrode belt, therefore said electrode belt can be detached and replaced by various belts to personalize belt size to chest size and gender.

According to an embodiment of the invention, the wire of the flying electrode is a spool with an outside electrically conductive electrode surface to allow the winding of the wire into the electrode compartment similar to a child's YOYO.

DETAILED DESCRIPTION OF THE INVENTION

The following description relates to embodiments of an electrocardiographic (ECG) monitoring system and method of the present invention by way of illustration only. It should be noted that from the following discussion, alternative embodiments of the structures and methods disclosed herein will be readily recognized as viable alternatives that may be employed without departing from the principles of the claimed invention.

Reference will now be made to several embodiments of the present invention(s), examples of which are illustrated in the accompanying figures. Wherever practicable similar or like reference numbers may be used in the figures and may indicate similar or like functionality. As aforementioned hereinabove, the figures depict embodiments of the present invention for purposes of illustration only. One skilled in the art will readily recognize from the following description that alternative embodiments of the structures and methods illustrated herein may be employed without departing from the principles of the invention described herein.

Unless otherwise indicated, the functions described herein may be performed by executable code and instructions stored in computer readable medium and running on one or more processor-based systems. However, hardwired electronic circuits can also be utilized. Further, with respect to the example processes described herein, not all the process states need to be reached, nor do the states have to be performed in the illustrated order. Further, certain process states that are illustrated as being serially performed can be performed in parallel.

Similarly, while certain examples may refer to a smartphone, other computer or electronic systems can be used as well, such as, without limitation, a network-enabled personal digital assistant (PDA), computer, communication hub or data device with an operating system and on which a user can install applications and so on.

In addition, while certain user inputs or gestures are described as being provided via phone key presses, data entry via a keyboard, the use of touch screens or by clicking a button, optionally, user inputs can be provided using other techniques, such as by voice or otherwise.

Figure 1:
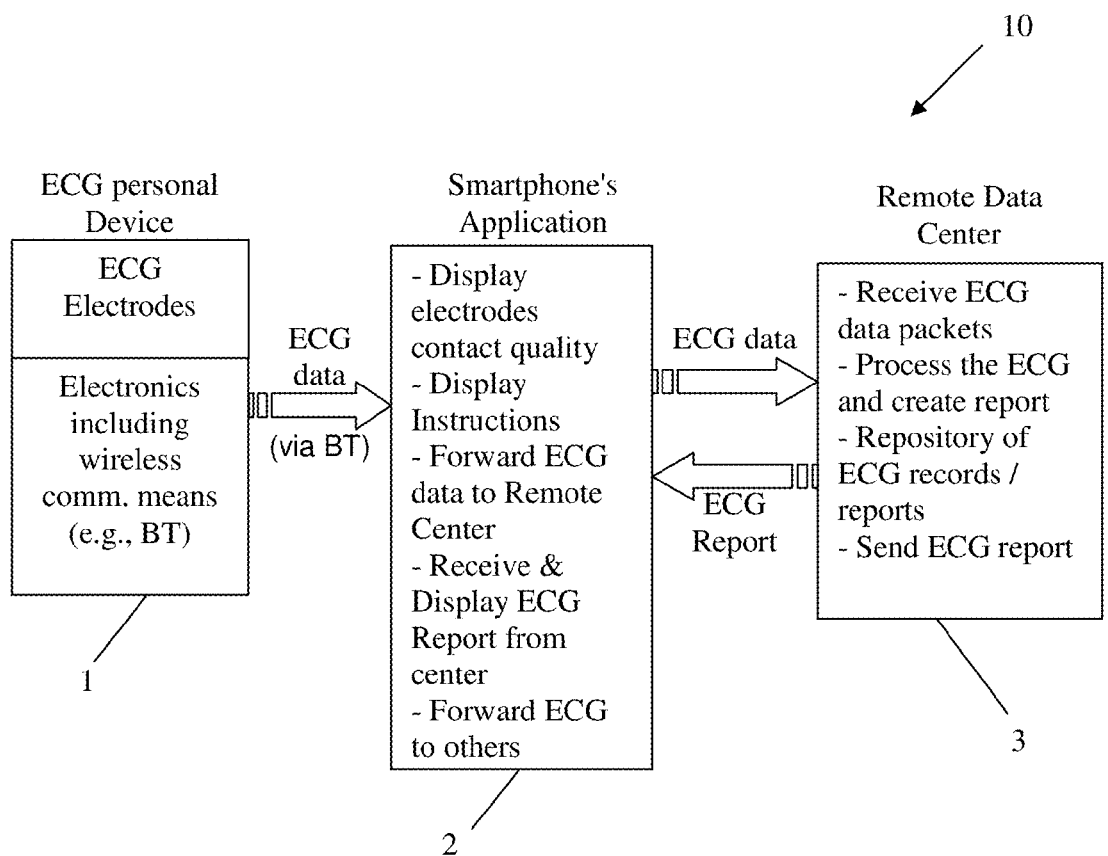
FIG. 1 schematically illustrates a layout of the personal ECG electrocardiographic monitoring system, according to an embodiment of the present invention.

FIG. 1 schematically illustrates a layout of an ECG monitoring system 10, according to an embodiment of the present invention. System 10 enables an individual to immediately gather and transmit 12-lead ECG and a rhythm strip data to a remote unit or to any required destination. The system 10 provides data which represents the electrical activity of the heart. The 12 Lead ECG defines the graphic representation of the electrical activity of the heart from various anatomical locations of the body. The electrical activity of the heart recorded over time is called a rhythm strip. The system 10 and its components are described in further details herein below.

System 10 comprises three main components: a personal ECG device 1, an application installed on a suitable mobile communication device 2 (e.g., an iPhone application) and a remote data center 3 with a dedicated software (e.g., the SHL medical monitoring center of SHL Telemedicine, remote medical center, or any other data center).

The personal ECG device 1 comprises skin electrodes and electronic components which are used for real-time transmission of the electrical activity of the heart as acquired by the skin electrodes. Device 1 transmits the data representing the electrical activity of the heart via a wireless communication link (e.g., via Bluetooth) to the mobile communication device 2.

According to an embodiment of the present invention, the electrocardiogram is constructed in the remote data center 3. The construction of the ECG and the operation of the remote data center 3 involve the following tasks:

receiving ECG data packets (from the mobile communication device) and performing error checking (by using any suitable error control technique that enables reliable delivery of digital data over communication channels);

processing the ECG data and creating a 12 lead ECG and/or Rhythm strip report/record;

storing the ECG records; and upon request, sending ECG reports and/or other related data in a variety of forms to other data devices (e.g., fax, email, printer, mobile phone, smartphone, etc).

In some uses, it is advantageous for the user to be able to capture and visualize their own ECG and then forward it to their doctor or another medical facility. By utilizing a smartphone, the system 10 of the present invention allows the user to acquire the ECG, visualize the ECG report (as delivered from the remote data center 3) on a smartphone and further, utilizing the smartphone allows the user to forward the electrocardiogram to a medical expert, his own doctor, or to a remote facility for analysis and/or advice.

According to some embodiments of the invention, ECG related activity can be conveyed to the user via the display unit of the smartphone. These may further include indication regarding the quality of the electrode contact and other relevant information (e.g., guiding and instructions for the user during and/or after the use), to be discussed in greater details below.

Figure 2:
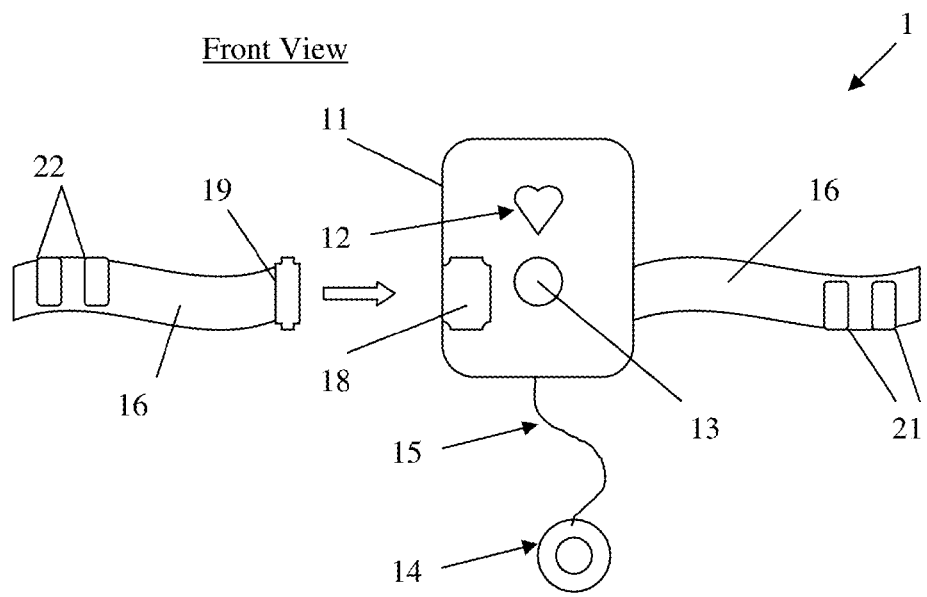
FIG. 2 schematically illustrates a front view of a personal ECG device, according to an embodiment of the present invention.
Figure 3:
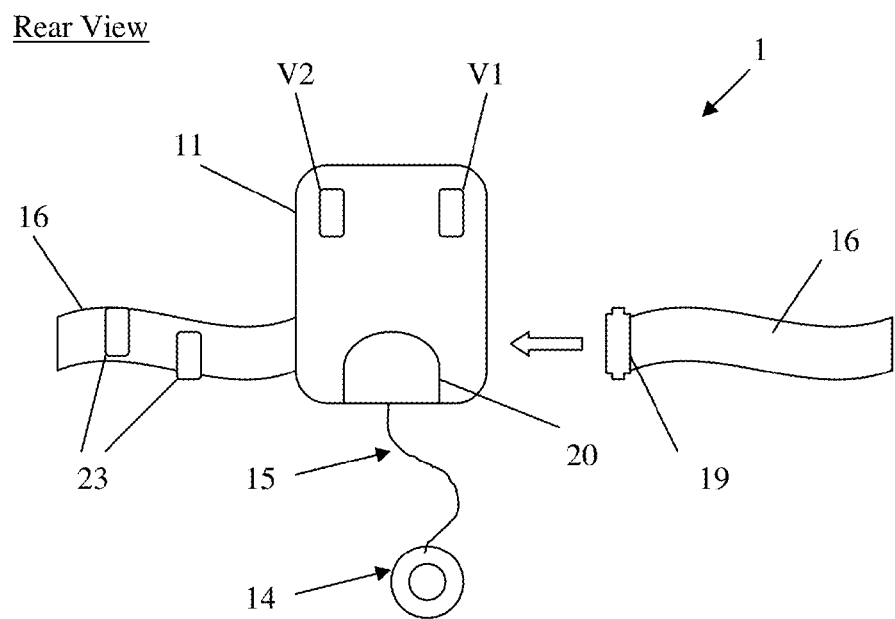
FIG. 3 schematically illustrates a rear view of the personal ECG device of FIG. 2.

FIGS. 2 and 3 show a personal ECG device 1 that can be used in conjunction with the invention. The device 1 illustrated in this figures is particularly convenient because it has a relatively small dimension and wherein its housing 11 is configured in such a way that it contains on its front panel a visual indicator 12 (e.g., in form of a glowing heart), which displays the status of the personal ECG device 1. Device 1 further comprises a "start" button 13 which used for turning "on" (or "off") the personal ECG device 1 (e.g., the "start" button can be located adjacent to the visual indicator 12). Preferably, the visual indicator 12 should be located on the front side of the housing of the personal ECG device 1 or on other location that will be seen easily by the user. This visual indicator 12 displays the status of the personal ECG device 1, whether it is turned on, measuring or has an error.

Device 1 further comprises a set of skin electrodes, wherein some of them are deployed along an electrode belt 16 (such as the exemplary electrodes indicated by numerals 21, 22 and 23), while other electrodes V1 and V2 are attached to the rear side of the housing 11 (see FIG. 3).

According to an embodiment of the invention, the device 1 also comprises a waist electrode 14 that is electrically connected to device 1 through a novel and unique retractable mechanism (i.e., a yoyo-like mechanism), as will be described in further herein after. The housing 11 of device 1 includes a compartment 20 adapted to store the waist electrode 14 while it is not in use. In this embodiment, the compartment 20 is located at the rear side of the housing 11, as easily seen in FIG. 3. This arrangement provides a compact and comfortable solution to the storage of the waist electrode 14. An advantage of the present invention over the prior art is that it utilizes only one flying electrode, which eliminates the possibility transposing flying electrodes which a can be a problem with devices that use multiple flying electrodes. Another advantage of the present invention over the prior-art devices is that the case of the flying electrode 14 is a spool with an outside electrically conductive electrode surface to allow the winding of the wire into the wire storage compartment after the use, due to the retractable mechanism that is configured to function in a similar manner as a child's YOYO.

Figure 6:
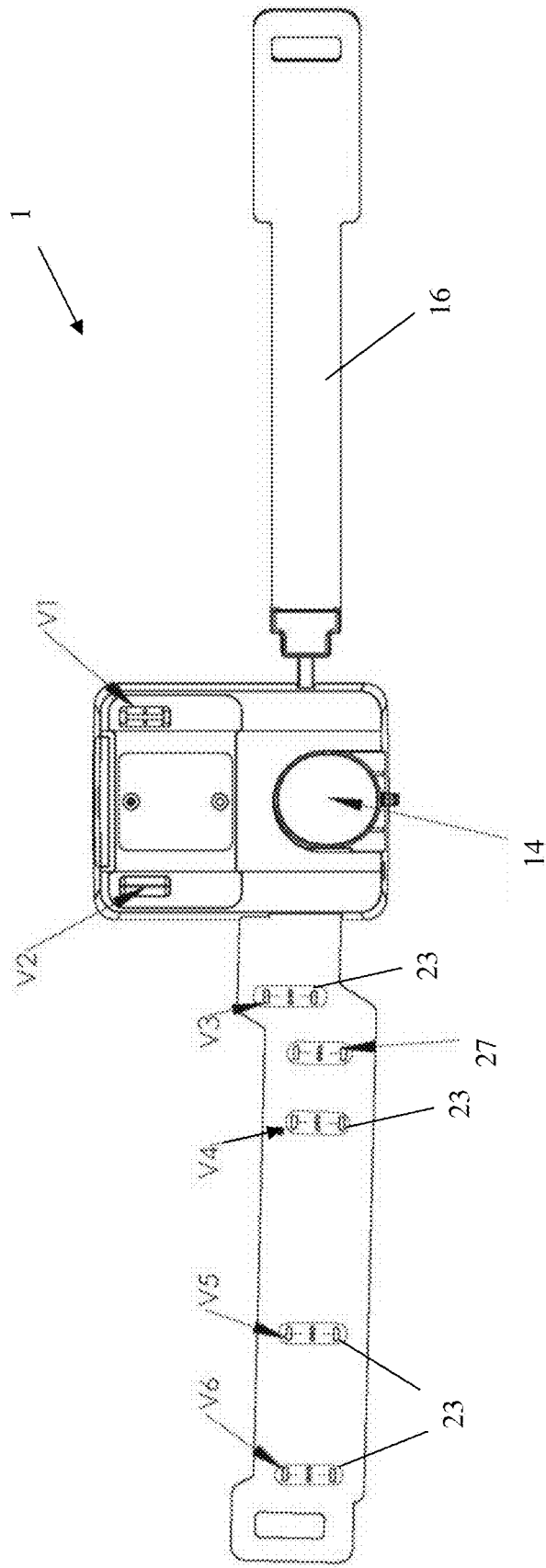
FIG. 6 schematically illustrates a rear view of the personal ECG device of FIG. 5.

In this embodiment, the rear side of the housing 11 has two electrodes (i.e., precordial electrodes as indicated by V1 and V2 in FIGS. 3 and 6). The housing 11 should be placed against the center of the user's chest. The housing's ergonomic design ensures the correct positioning of the electrodes V1 and V2 against the chest, while affording the user maximum comfort with minimal exertion when operating the device.

The device 1 further comprises a belt closure arrangement as indicated by elements 18 and 19 for closing the belt 16, while it surrounds the body of the user. According to an embodiment of the invention, in addition to the mechanical attachment, the buckle (element 19) and the corresponding belt closure (element 18) are also electrically connected. For example, electrical wirings (not shown) can be used to connect each of the skin electrodes 21 and 23 (that are deployed along belt 16), while the electrical connection between the belt's buckle 19 and the corresponding closure 18 allows to transfer the electrical activity of the heart as acquired by the skin electrodes 22 to the electronic components of device 1.

The personal ECG device 1 is powered by a power source such as one or more batteries. For example, the batteries can be 2 lithium "AAA" batteries. Alternatively, alkaline batteries can also be used.

Figure 4:
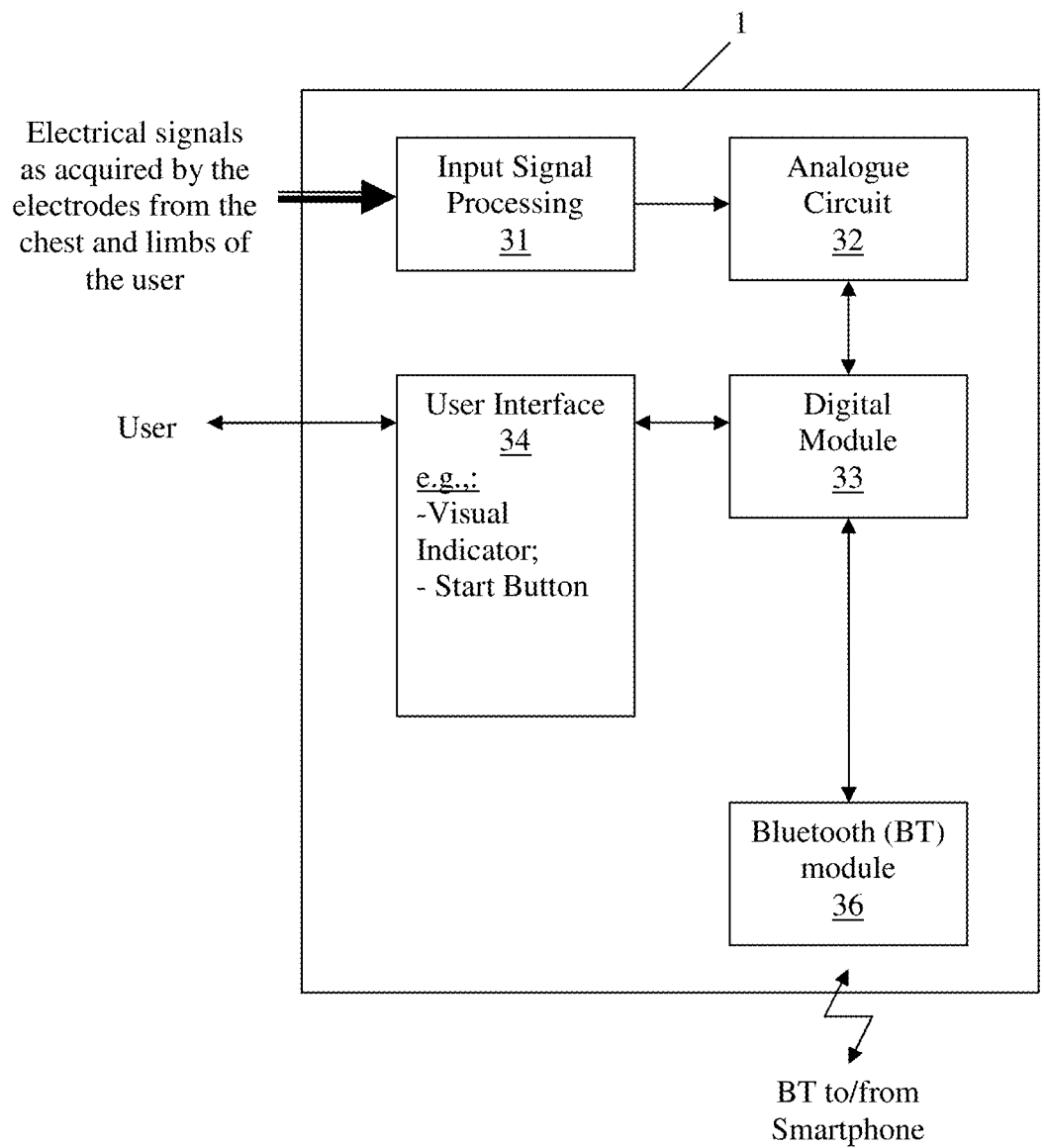
FIG. 4 schematically illustrates an electronic block diagram of the personal ECG device, according to an embodiment of the present invention.

Referring now to FIG. 4, a schematic layout of the electronic components within the housing 11 of the personal ECG device 1 is shown in accordance with an embodiment of the present invention. The electronic components that are located inside the housing 11 of device 1 are divided to two main electronic modules: an analog module 32 and a digital module 33.

The input signal processing module 31 contains signal conditioning circuitry to acquire the low level electrical signals from the electrodes. The signals from the electrodes are acquired in the Analogue Circuit 32 in such a manner to obtain the data for the standard Einthoven limb leads, the Goldberger augmented leads and the Wilson precordial leads which comprise the standard 12 lead electrocardiogram. For example, the signal condition circuitry may include typical electronic components for amplifying the low level electrical signals 31 from the electrodes and to convert them into a digital form in the Digital Module 33, such as input amplifiers, analog to digital converters, filters, and/or other components that can be used to manipulate analog signals.

The digital module 33 digitizes the electrocardiographic signals. Further this module also provides the two way wireless communication protocol to convey all the digital data to and from the mobile communication device 2 (e.g., a wireless communication between the device 1 and an iPhone, iPad, iTouch, other smartphones or wireless communication devices via a Bluetooth (BT) module 36 or other wireless protocol). Device 1 further comprises a user interface (UI) 34 or other Man Machine Interface, which may include one or more visual indicators (e.g., the glowing heart indicator light 12) and/or other display unit (e.g., LCD panel), one or more functional button (e.g., such as the start button 13), etc.

One of the advantages of the personal ECG device of the present invention with respect to prior-art devices is that it needs to transmit data to a paired and relatively adjacent portable communication device, such as a smartphone (using short range data communication protocol, e.g., Bluetooth). Short range transmissions reduce power consumption. Accordingly, the personal ECG device requires a smaller battery, which leads to its relatively smaller dimensions (e.g., about 8.5 cm width, 11 cm length and 1.5 cm height). A smaller battery also results in a lighter unit (e.g., about 100 g). Lower power consumption also allows the practical use of disposable batteries, eliminating the need for a recharger with cable. All these factors further reduce the size and weight of a user's carrying/storage package.

Electrodes

The device housing and belt contain electrodes (i.e., set of skin electrodes) for acquiring electrical signals from the conventional anatomic electrode locations for a standard 12 lead electrocardiogram from the chest and limbs. For example, the electrodes can be made from PC ABS+20% glass fiber with a coating of silver/silver chloride (Ag/AgCl).

Usually several electrodes are used and they can be combined into a number of pairs (e.g., left arm and right arm electrodes). The output from each combination is known as a lead. Each lead is said to look at the heart from a different angle. A 12-lead ECG is a recording of the heart's electrical activity from 9 anatomically located electrodes on the body which are combined to produce a conventional clinical 12-lead report.

Figure 5:
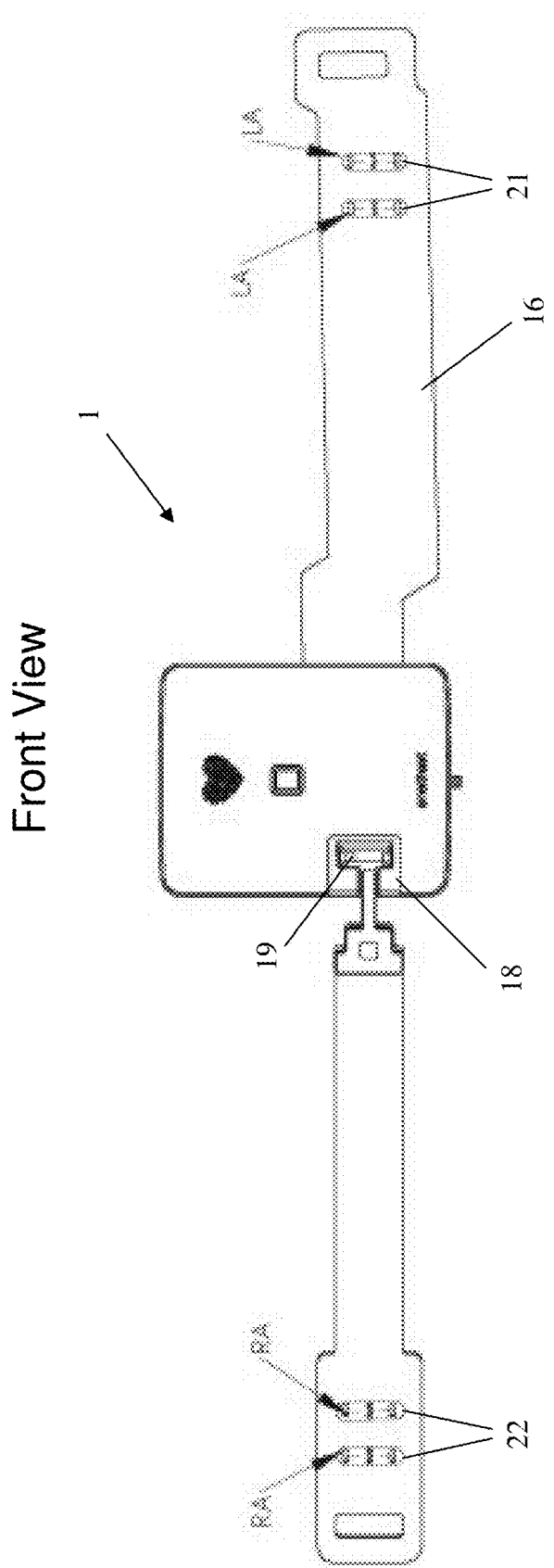
FIG. 5 schematically illustrates a front view of a personal ECG device provided with an electrodes belt, according to an embodiment of the present invention.

Referring now to FIGS. 5 and 6, a personal ECG device with electrodes belt is shown in accordance with an embodiment of the present invention. In this embodiment, the electrodes Location deployed as follows: two electrodes are located on the housing (indicated by V1 & V2), four precordial electrodes are located on the left electrode belt (indicated by V3 to V6, two limb electrodes consisting of Left Arm (LA), Right Arm (RA) belt mounted electrodes and a flying lead Left Leg (LL) (waist) retractable limb electrode (i.e., the waist electrode 14 with the yoyo-like mechanism (not shown in rear view FIG. 6) attached via a conductive wire.

According to an embodiment of the present invention, the belt can be detached from the housing of the personal ECG device. For example, there can be plurality of belts sizes in order to accommodate variety of chest sizes, wherein each one of them is designed for a specific gender and body size. By replacing the belt, the personal ECG device can fit all users. To accommodate different chest sizes, different belts with strategically positioned electrodes can be used for each gender.

According to an embodiment of the present invention, the electrode belt comprises a dual purpose belt closure: An interlocking fastener is attached to the belt. This permits the user to mechanically attach the end of the chest belt to the housing. Further, this fastener contains electrical contacts to electrically connect some belt monitoring electrodes to the electronics of the device as will be described in further details herein after in the electrodes belt section.

According to an embodiment of the present invention, the personal ECG device is provided with a dual purpose belt closure (as shown in FIGS. 5 and 6). The electrode belt includes electrical wiring for electrically contacting the electrodes via the belt closure to the electronics of the personal ECG device.

In this embodiment, the electrode belt is an elastic chest strap which comprises 6 precordial ECG electrodes, Right/Left Arm electrodes (indicated by RA and LA in FIG. 5) and a unique, convenient belt closure 18 containing electrical connections to electrically connect with buckle 19 (in addition to their mechanical engagement while fastening the belt around the user's chest).

In general, in order to obtain a 12 lead electrocardiogram, at least 9 electrodes are required to be positioned on the user's body. Six of the electrodes are precordial electrodes that a positioned at certain anatomical electrode locations on the chest (as indicated by electrodes V1-V6 in FIG. 6). The remaining 3 electrodes are limb electrodes monitor the electrical signals on the left arm (LA electrode), right arm (RA electrode) and the left leg (i.e., the retractable waist electrode). For simplicity of use, as aforementioned herein before the personal ECG device has 2 precordial, chest-facing electrodes on the electronic enclosure case (i.e., on the rear side of the housing) and the remaining 4 precordial electrodes are on the belt itself. In addition, two limb electrodes Right Arm (RA) and Left Arm (LA) outward facing electrodes. To easily apply the elastic belt, the electrode belt is permanently attached to the electronic enclosure and the other end is fitted with a novel closure/snap. In this way, when the mechanical belt fastener is engaged with the case, an electrical connection is also achieved to the RA sensing electrodes.

According to an embodiment of the invention, the electrodes belt further includes a body reference electrode as indicated by numeral 27 in FIG. 6. The body reference electrode 27 provides a reference for the input amplifiers of the signal conditioning circuitry, which contributes to reduction of mains noise and better performance.

For example, the electrodes belt can be made from neoprene covered with Nylon fabric which is the same material utilized for wet suits. This is a comfortable and soft material, ideal for repeated flexing applications. Two electrodes belts are connected with stretch belt.

The left part of the electrode belt is permanently attached to the left side of the housing and contains several monitoring electrodes: e.g., five electrodes (4 precordial monitoring electrodes and one amplifier reference electrode) on the inside of the belt and a further two limb electrodes (i.e., a duplication of electrodes to monitor LA (Left Arm) on the outside. The right part of the electrode belt contain two electrodes on the outside, both are for the RA right arm connection. The right electrode belt has a double contact buckle that insures good electrical connection between the electrodes and the housing. The two parts of the electrode belt are connected with stretch belt between them. To accommodate different chest sizes, there are different size belts. The belts have electrodes positioned in the optimal position for each chest size, such that one or more electrodes may have more than one contact deployed along the belt.

YOYO "Flying" Electrode

According to an embodiment of the present invention, the personal ECG device further comprises an electrode attached with wire to the bottom of the housing (referred to as "flying" electrode). This "flying" electrode is labeled 'waist', referring to where it should be placed. The flying ('waist') is positioned at the user's belt line against the bare skin, halfway from the navel to the left hip. Together with the electrodes on the front of the electrode belts, these make up the three limb electrodes. The limb electrodes and the other electrodes on the belt in combination with those on the housing device permit the acquisition of ECG data for a rhythm strip and 12 lead ECG for remote interpretation by a qualified healthcare professional.

The flying electrode has wire a spool or retractor that collect the entire waist electrode wire into the electrode compartment. Using this retractor enables the compact packing of the waist electrode. When the device is not in use, there is no electrode wire hanging outside the housing as occur in prior art devices.

Smartphone Application

The example screen layouts, appearance, and terminology of Smartphone application as depicted and described herein with respect to FIGS. 7-11, are intended to be illustrative and exemplary, and in no way limit the scope of the invention as claimed.

The application may include the following options or application menus:

Symptoms menus—the application can display menus of predefined selectable symptoms so that the user can select any present symptoms.

Figure 7:
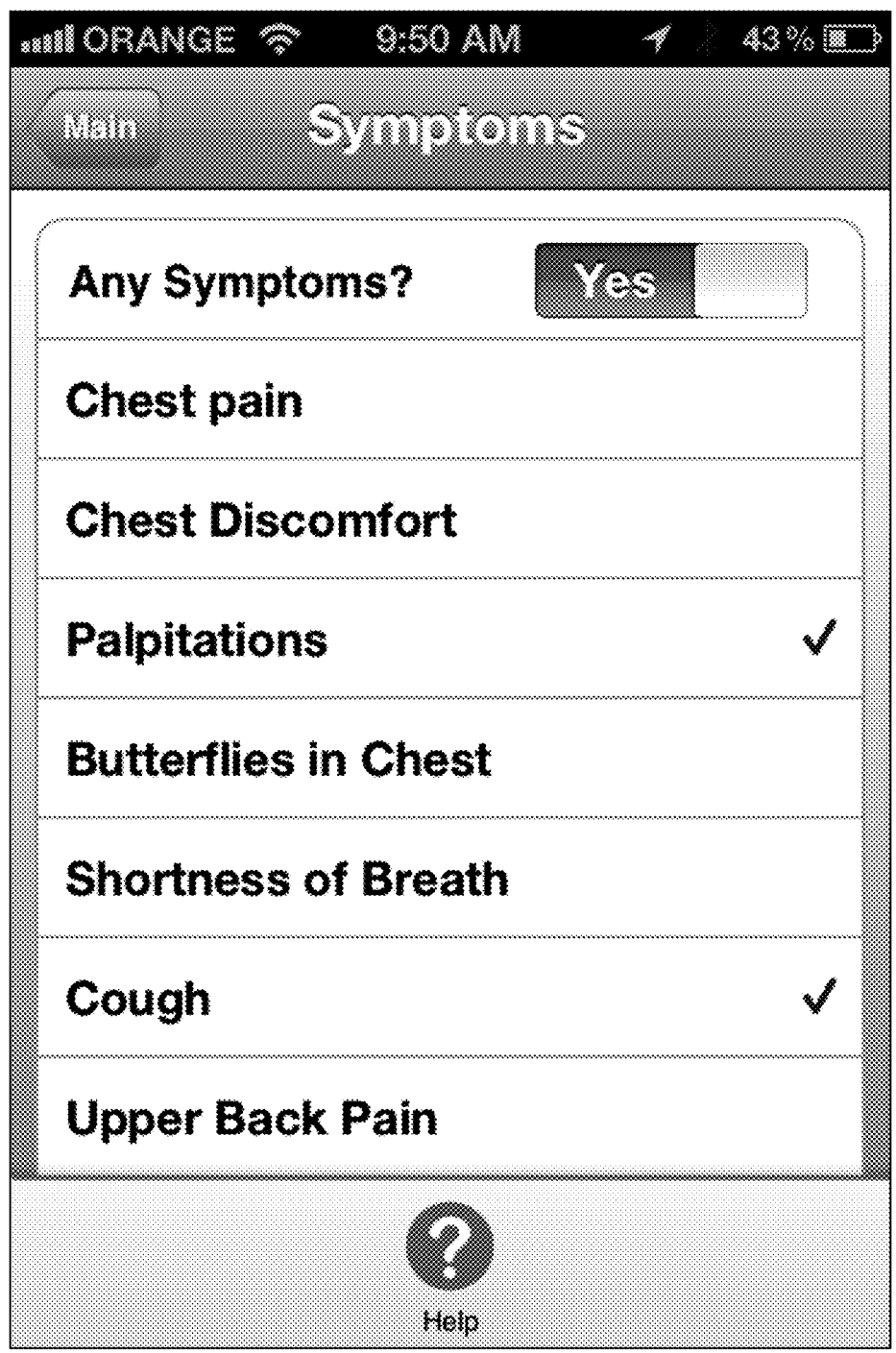
FIGS. 7-11 schematically illustrate example Smartphone screen layouts of a dedicated application to be used with the personal ECG device, according to an embodiment of the present invention.

Perform an ECG—This permit selecting symptoms and recording an ECG including a screen to display the electrode status and guide the user in how to position the electrodes. FIG. 7 shows a graphical example screen of a symptom menu of the smartphone application.

Figure 8:
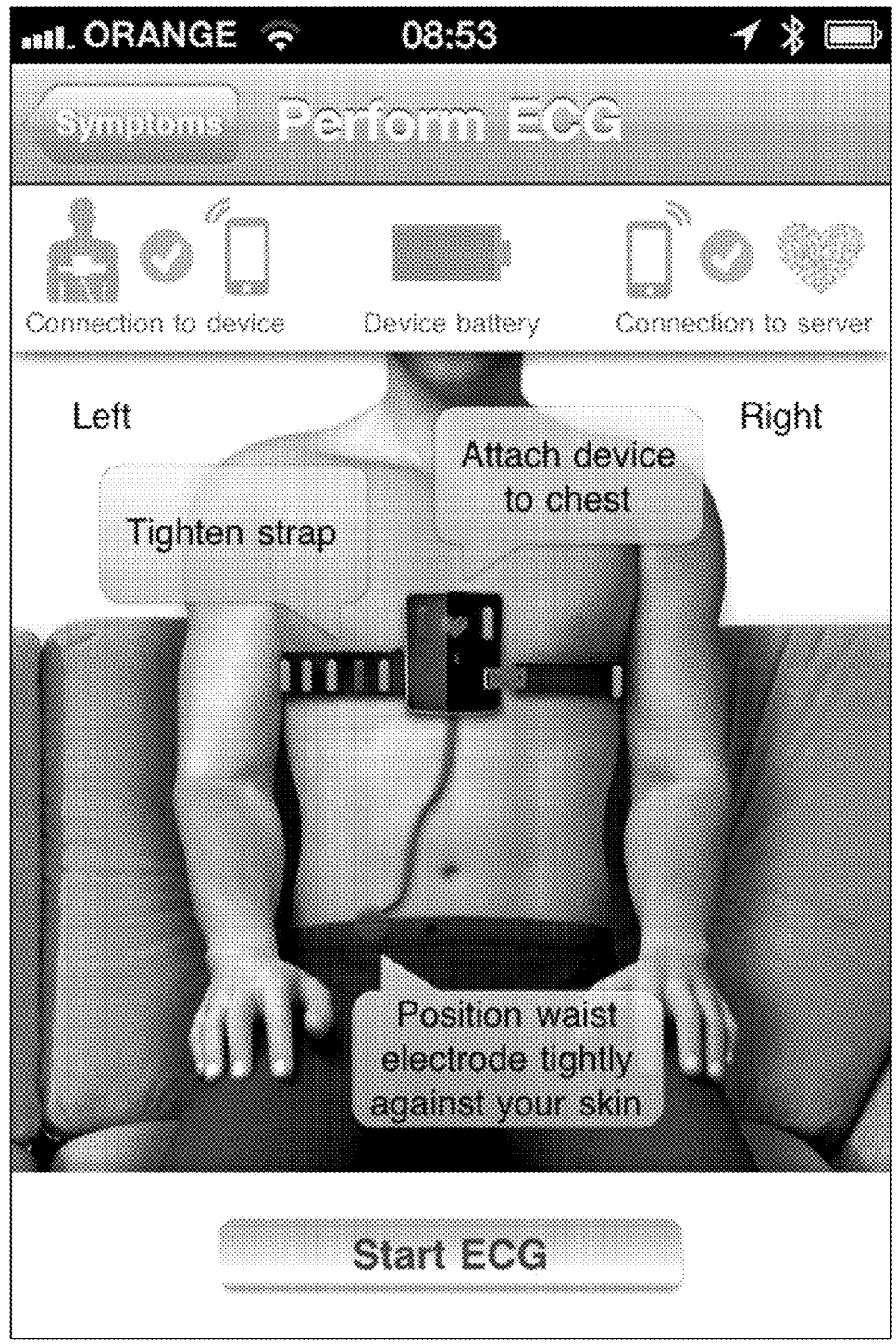

Electrodes Contact Quality Display—FIG. 8 shows a graphical example of electrodes contact quality screen of the smartphone application. This screen displays the contact status of the electrodes and will guide the user to correctly position the electrodes in order to improve the contact of the electrodes with the user's body, for example, by displaying visual messages on the displayed image of the human chest (when the personal ECG device is not position correctly), such as "position waist electrode tightly against your skin", "attach device to chest", "tighten strap", etc.

Figure 9:
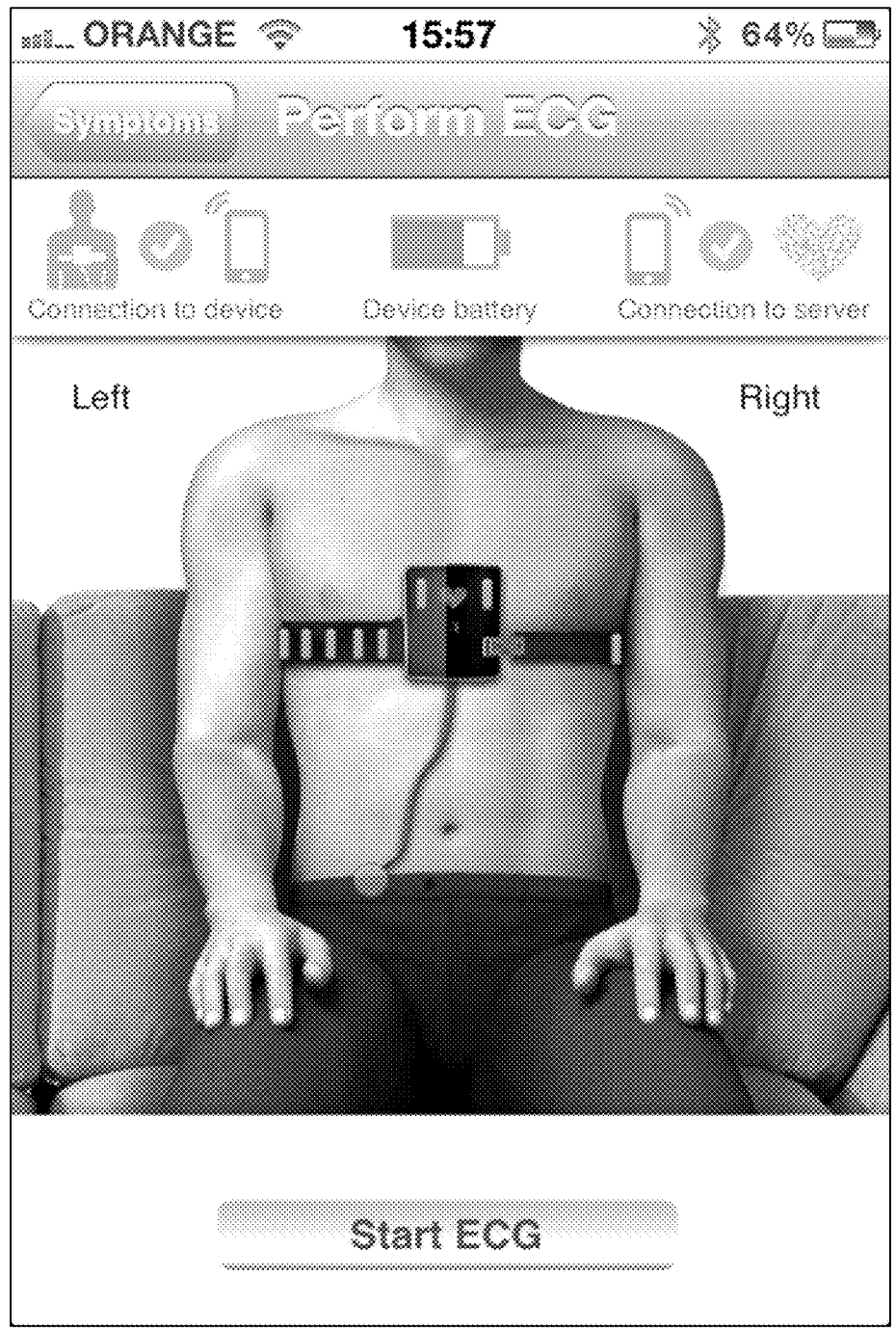

ECG recording progress—FIG. 9 shows a graphical example of the ECG perform starting screen of the smartphone application. This screen shows an indication that all the electrodes are in contact (i.e., which is an essential information before the beginning of the recording progress).

Figure 10:
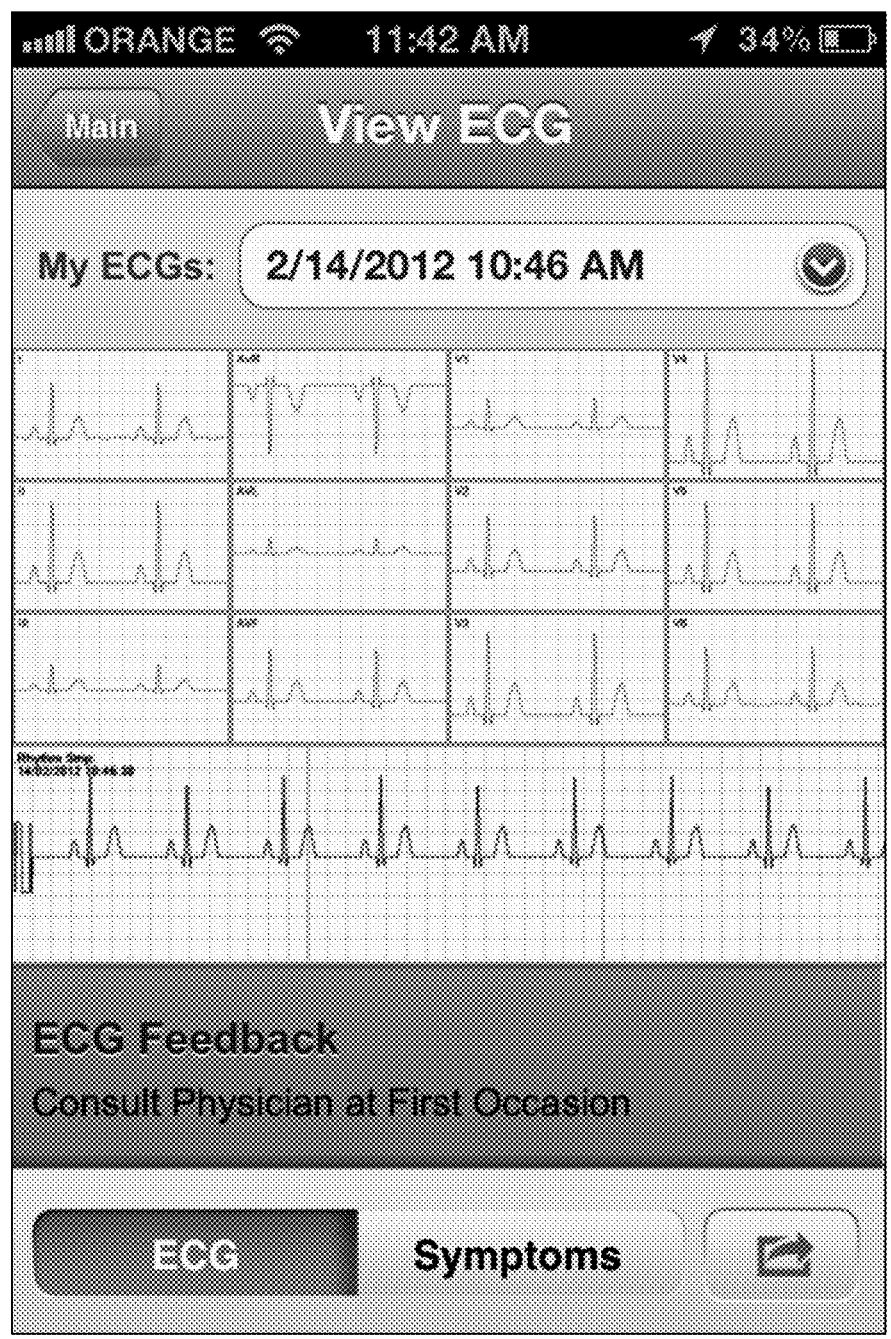

Viewing ECGs—FIG. 10 shows a graphical example of recorded ECGs screen of the smartphone application. This screen permits the viewing reports of the recorded ECGs.

Figure 11:
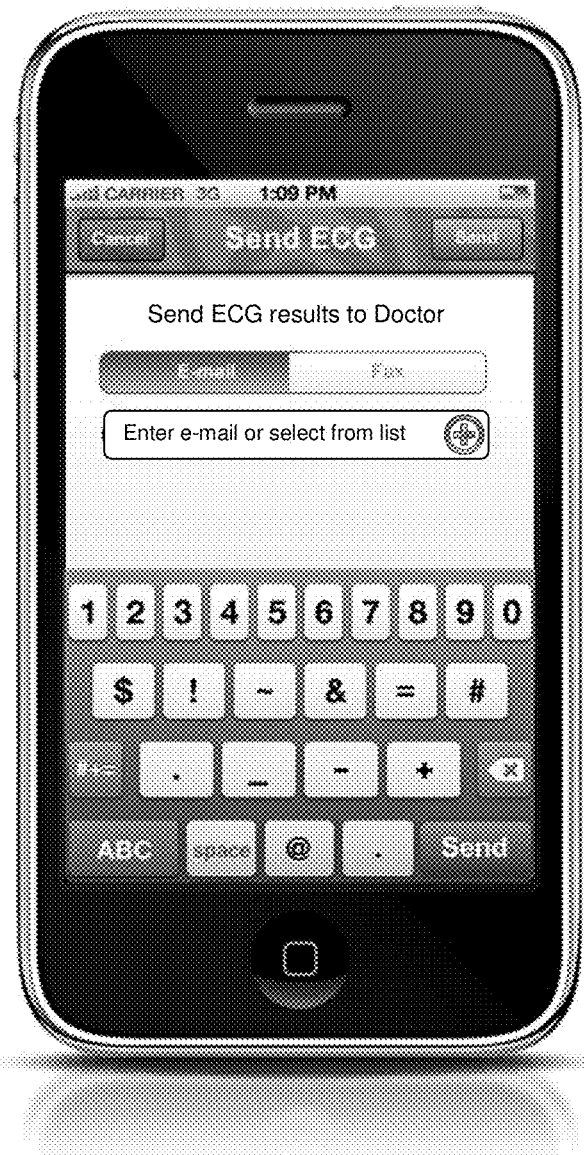

Sending ECG—FIG. 11 shows a graphical example of Send ECGs screen of the smartphone application. This screen permits the forwarding of ECGs, e.g., via e-mail or fax.

Help Function—This includes training information for using the personal ECG device, using the smartphone application and information about the symptoms.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

Moreover, the terms, "for example", "e.g.", "optionally", as used herein, are intended to be used to introduce non-limiting examples. While certain references are made to certain example system components or services, other components and services can be used as well and/or the example components can be combined into fewer components and/or divided into further components.

The invention claimed is:

1. A device for obtaining a standard 12-lead electrocardiogram (ECG) and a rhythm strip, comprising:
   a. a personal ECG device having a housing, comprising a front side and a rear side, that includes an analog input signal processing module adapted for acquiring low level electrical signals from skin monitoring electrodes, a digital module for converting the acquired signals into digital data form, and a communication module for establishing a wireless communication between said personal ECG device and a mobile communication device, thereby enabling to convey data between both devices including the transferring of said converted digital data to said mobile communication device; and b. 9 skin monitoring electrodes suitable to be positioned on the body of a user in a standard 12 lead anatomical manner in accordance with Einthoven, Goldberger and Wilson, wherein said standard 12 lead anatomical manner is obtained by deploying said electrodes along a belt connected with said personal ECG device and on the rear side of the housing of said personal ECG device, wherein at least some of said skin electrodes are precordial electrodes located on the inside of said belt and positioned on the chest of said user, two electrodes that are belt-mounted limb electrodes located on the outside of said belt, said two belt-mounted electrodes acquiring electrical signals of the left arm (LA electrode) and the right arm (RA electrode), and 1 flying electrode (LL electrode), said flying electrode acquiring the electrical signals of the left leg of said user.

2. A device according to claim 1, in which the mobile communication device establishes data communication with a remote data center for transmitting the data to said remote data center for processing and creating a 12 lead ECG and rhythm strip report at said remote center.

3. A device according to claim 2, in which the mobile communication device establishes data communication with the remote data center while in voice contact with a representative of said remote data center.

4. A device according to claim 2, in which the mobile communication device is operable to receive from the remote data center the created 12 lead ECG and rhythm strip report, thereby enabling a user to observe a representation of the 12 lead ECG and the rhythm strip report on the display of the mobile communication device.

5. A device according to claim 1, in which the wireless communication between the personal ECG device and the mobile communication device enables a user to improve the contact quality of the electrodes by using the mobile communication device to display the contact quality of each skin monitoring electrode, thereby providing feedback to the user to evaluate the quality of the electrode contact and permitting said user to improve the contact and thus the quality of the resulting ECG.

6. A device according to claim 1, in which the mobile communication device provides instructions, questions, or other relevant data to a user while operating the personal ECG device.

7. A device according to claim 1, in which the housing includes a belt closure arrangement for mechanically securing the belt while it surrounds the body of the user, and for electrically connecting at least some of the electrodes of said belt to the analog input signal processing module.

* * * * *